US00PP14708P2

(12) United States Plant Patent
Hansson

(10) Patent No.: US PP14,708 P2
(45) Date of Patent: Apr. 20, 2004

(54) OSTEOSPERMUM PLANT NAMED 'SEVAMIL'

(50) Latin Name: *Osteospermum ecklonis*
Varietal Denomination: Sevamil

(76) Inventor: Jorn Hansson, Holmevej 36, 5471 Sondersoe (DK)

( * ) Notice: Subject to any disclaimer, the term of this patent is extended or adjusted under 35 U.S.C. 154(b) by 0 days.

(21) Appl. No.: 10/408,182

(22) Filed: Apr. 6, 2003

(51) Int. Cl.[7] ..... A01H 5/00
(52) U.S. Cl. ..... Plt./360
(58) Field of Search ..... Plt./360

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Osteospermum plant named 'Sevamil', characterized by its compact, mounded and outwardly spreading plant habit; freely branching growth habit; freely flowering habit; and pale yellow-colored ray florets and dark purple-tipped disc florets.

1 Drawing Sheet

Botanical classification/cultivar designation: *Osteospermum ecklonis* cultivar Sevamil.

BACKGROUND OF THE INVENTION

The present Invention relates to a new and distinct cultivar of Osteospermum plant, botanically known as *Osteospermum ecklonis,* and hereinafter referred to by the name 'Sevamil'.

The new Osteospermum was discovered as a naturally-occurring whole plant mutation of the *Osteospermum ecklonis* cultivar Seikilrem, disclosed in U.S. Plant Pat. No. 13,407.

The new Osteospermum was discovered and selected by the Inventor in June, 2000, as a single flowering plant within a population of plants of the parent cultivar in a controlled environment in Sondersoe, Denmark.

Asexual reproduction of the new Osteospermum by terminal vegetative cuttings was first conducted in Sondersoe, Denmark in August, 2000. Asexual reproduction by cuttings has shown that the unique features of this new Osteospermum are stable and reproduced true to type in successive generations.

SUMMARY OF THE INVENTION

The cultivar Sevamil has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sevamil'. These characteristics in combination distinguish 'Sevamil' as a new and distinct Osteospermum:

1. Compact, mounded and outwardly spreading plant habit.
2. Freely branching growth habit.
3. Freely flowering habit.
4. Pale yellow-colored ray florets and dark purple-tipped disc florets.

Plants of the new Osteospermum are most similar to plants of the parent, the cultivar Seikilrem. Plants of the new Osteospermum differ primarily from plants of the cultivar Seikilrem in ray floret coloration as plants of the cultivar Seikilrem have bright yellow-colored ray florets.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photograph at the top of the sheet comprises a side perspective view of a typical flowering plant of 'Sevamil' grown in a 15-cm container.

The photograph at the bottom of the sheet is a close-up view of typical inflorescences, inflorescence buds and leaves of 'Sevamil'.

DETAILED BOTANICAL DESCRIPTION

The aforementioned photographs and following observations and measurements describe plants grown in Bonsall, Calif., in an outdoor nursery during the late spring and early summer under full sun conditions with day temperatures ranging from 18 to 35° C. and night temperatures ranging from 7 to 18° C. After planting rooted cuttings, plants were grown for about six weeks in 15-cm containers. Color references are made to The Royal Horticultural Society Colour Chart, 1995 Edition, except where general terms of ordinary dictionary significance are used.

Botanical classification: *Osteospermum ecklonis* cultivar Sevamil.

Parentage: Naturally-occurring whole plant mutation of the *Osteospermum ecklonis* cultivar Seikilrem, disclosed in U.S. Plant Pat. No. 13,407.

Propagation:

*Type.*—Terminal vegetative cuttings.

*Time to initiate rooting.*—About 14 days at 20° C.

*Time to develop roots.*—About 28 days at 20° C.

*Root description.*—Fine, fibrous and well-branched.

Plant description:

*Appearance.*—Perennial herbaceous container and garden plant. Compact and mounded plant habit; initially upright and then outwardly spreading. Freely branching, about 16 lateral branches develop after pinching; dense and full plants. Vigorous growth habit.

*Plant height.*—About 25 cm.

*Plant width or area of spread.*—About 46 cm.

*Lateral branches.*—Length: About 25 cm. Diameter: About 4 mm. Internode length: About 1.5 cm. Aspect: Upright to outward. Strength: Strong. Texture: Glabrous. Color: 144B.

*Foliage description.*—Arrangement: Alternate; simple. Length: About 5.5 cm. Width: About 1.7 cm. Shape: Obovate. Apex: Rounded to broadly acute. Base: Attenuate. Margin: Entire. Venation pattern: Pinnate. Texture, upper and lower surfaces: Smooth, glabrous. Color: Developing foliage, upper surface: 146A. Developing foliage, lower surface: 146B. Fully expanded foliage, upper and lower surfaces: 146B. Venation, upper surface: 147D. Venation, lower surface: 147C. Petiole: Length: About 5 mm. Diameter: About 2 mm. Texture, upper and lower surfaces: Glabrous. Color, upper and lower surfaces: 147D.

Inflorescence description:

*Appearance.*—Terminal and axillary inflorescences held above and beyond the foliage on moderately strong peduncles. Composite inflorescence form, radially symmetrical, with ligulate-shaped ray florets and disc florets massed at the center; ray and disc florets arranged acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about five to ten days on the plant when grown in an outdoor environment.

*Quantity of inflorescences.*—Freely flowering; at one time, about seven to ten open inflorescences and inflorescence buds per lateral stem.

*Fragrance.*—None detected.

*Inflorescence bud* (*at stage of showing color*).—Length: About 1.5 cm. Diameter: About 8 mm. Shape: Ovoid. Color, ray florets, lower or outer surface: 2A.

*Inflorescence size.*—Diameter: About 5.5 cm. Depth (height): About 1.75 cm. Disc diameter: About 8 mm. Receptacle diameter: About 1.3 cm. Receptacle height: About 1 cm.

*Ray florets.*—Length: About 2.8 cm. Width: About 6 mm. Shape: Ligulate. Apex: Emarginate. Base: Acute. Margin: Entire. Texture, upper and lower surfaces: Smooth, satiny. Orientation: Initially upright then about 45 to 60° from vertical. Number of ray florets per inflorescence: About 18 in one whorl. Color: When opening, upper surface: 11D. When opening, lower surface: Ground color, 12C, with fine longitudinal stripes, 191B to 191C. Fully opened, upper surface: 11D; towards base, 79B to 79C; color fading to close to 155D with development. Fully opened, lower surface: Ground color, 13B, with fine longitudinal stripes, 191C to 191D.

*Disc florets.*—Shape: Tubular, elongated. Apex: Five-pointed. Length: About 9 mm. Width: At apex: About 2 mm. At base: About 1 mm. Number of disc florets per inflorescence: About 70. Color: Immature: 146A tipped with 103A. Mature, apex: 14C tipped with 79A. Mature, mid-section and base: 155D.

*Phyllaries.*—Length: About 1 cm. Diameter: About 1 mm. Shape: Linear. Apex: Acuminate. Base: Fused. Margin: Entire. Texture, upper and lower surfaces: Slightly pubescent. Number per inflorescence: About 15 in a single whorl. Color, upper and lower surfaces: 146A.

*Peduncles.*—Length, terminal peduncle: About 8.5 cm. Length, third peduncle: About 9 cm. Length, fifth peduncle: About 6.5 cm. Diameter: About 1.5 mm. Angle: Terminal peduncles, erect; secondary and tertiary peduncles, about 45 to 60° from vertical. Strength: Moderately strong. Texture: Slightly glandular; smooth. Color: 144B.

*Reproductive organs.*—Androecium: Stamen number: Five per floret; fused around style. Anther shape: Oblong. Anther length: Less than 1 mm. Anther color: 103A. Pollen amount: Scarce. Pollen color: 23A. Gynoecium: Pistil number: One per floret. Pistil length: About 7 mm. Stigma shape: Two-parted. Stigma color: 79B. Style length: About 4 mm. Style color: 155A. Ovary color: 145A.

*Seed/fruit.*—Seed and/or fruit production has not been observed.

Disease/pest resistance: Resistance to pathogens and pests common to Osteospermum has not been observed on plants grown under commercial greenhouse or outdoor conditions.

Temperature tolerance: Plants of the new Osteospermum have been observed to tolerate temperatures from 4 to 35° C.

It is claimed:

1. A new and distinct cultivar of Osteospermum plant named 'Sevamil', as illustrated and described.

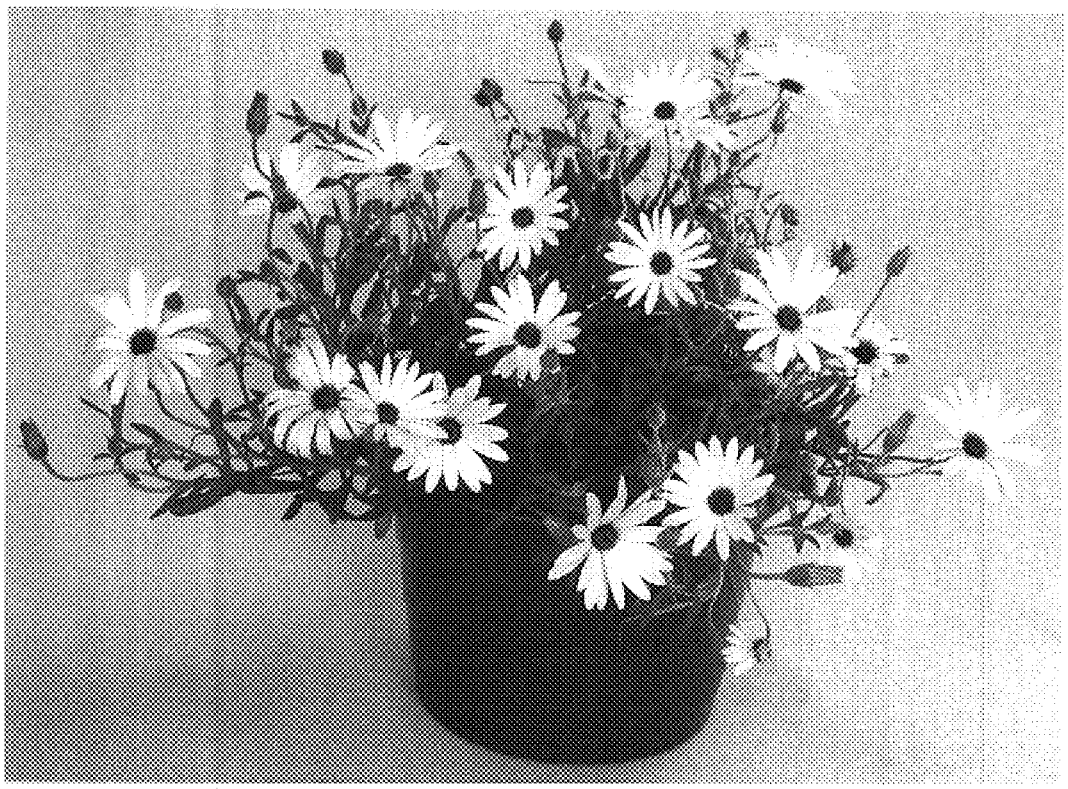
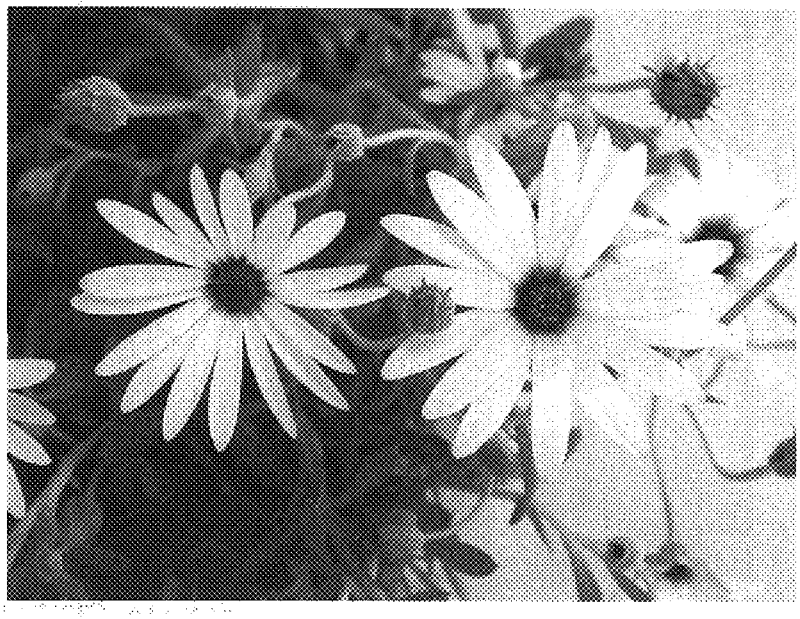

* * * * *